United States Patent
Neumann et al.

(10) Patent No.: US 6,573,394 B1
(45) Date of Patent: Jun. 3, 2003

(54) POLYOXOFLUOROMETALLATES AND USE THEREOF AS CATALYSTS FOR THE EPOXIDATION OF ALKENES

(75) Inventors: Ronny Neumann, Kfar Saba (IL); Alexander Khenkin, Maale Adumim (IL); Revital Ben-Daniel, Modiin (IL)

(73) Assignees: Yissum Research Development Company of Hebrew University of Jerusalem, Jerusalem (IL); Yeda Research and Development Company Ltd., Rehovot (IL)

( * ) Notice: Subject to any disclaimer, the term of this patent is extended or adjusted under 35 U.S.C. 154(b) by 0 days.

(21) Appl. No.: 09/936,025
(22) PCT Filed: Jan. 24, 2000
(86) PCT No.: PCT/IL00/00044
§ 371 (c)(1),
(2), (4) Date: Sep. 7, 2001
(87) PCT Pub. No.: WO00/43122
PCT Pub. Date: Jul. 27, 2000

(30) Foreign Application Priority Data

Jan. 24, 1999 (IL) .................................................. 128206

(51) Int. Cl.$^7$ ...................... C07D 207/00; C07D 209/04
(52) U.S. Cl. ...................... 549/523; 549/512; 549/513; 549/533; 549/535
(58) Field of Search ................................ 549/523, 533, 549/512, 535; 545/513

(56) References Cited

PUBLICATIONS

Sadiq et al, Inorg. Chem. 1991, 30 (8) pp. 1788–1792.*
Sadiq et al, Inorg. Chimica Acta, 1998, 268 (10) pp. 329–333.*
Jorris et al, Inorg. Chem. 1990, 29 (22) pp. 4584–4586.*

Thomas Lee Jorris: "Preparations, structures and properties of d, I–aquometallopolytungstopolyfluorosodate s, the first heteropoly complexes containing fluoride" Dissertation Abstracts International. B. The Science and Engineering, vol. 49, No. 7, Jan. 1989, p. 2639 XP000905127 Ann Arbor, US, ISSN: 0419–4217, Cited in the Application, Abstract.

Sadiq H. Wasfi, Catherine E. Costello, Arnold L. Rheingold, and Brian S. Haggerty: Preparation and characterization of two new isomorphous heteropolyoxofluorotungstate anions: 'CoW17056F6NaH4!9–and'Few 17056F6NaH4!8–Inorganic Chemistry., vol. 30, No. 8, Apr. 17, 1991, pp. 1788–1792, XP000905087 American Chemical Society. Easton., US ISSN: 0020–1669.

Sadiq H. Wasfi, Sandra A. Tribbitt: "Preparation and characterization of a new heteropolyoxofluorotungstate anion 'InW17056F6NaH4!8–"Inorganica Chimica Acta, vol. 268, No. 2, Feb. 10, 1998, pp. 329–333, XP000905199 Lausanne, CH ISSN: 0020–1693.

Thomas L. Jorris, Mariusz Kozik, and Louis C.W. Baker: "Reformulation of the hexafluorooctadecatungstate anion as a heteropoly sodate complex: 'H2F6NaW18056!7–" Inorganic Chemistry, vol. 29, No. 22, Oct. 31, 1990, pp. 4584–4586, XP000905191 American Chemical Society, Easton, US ISSN: 0020–1669.

* cited by examiner

Primary Examiner—Alan L. Rotman
Assistant Examiner—Hector M Reyes
(74) Attorney, Agent, or Firm—Morgan Lewis & Bockius LLP

(57) ABSTRACT

The invention provides a process for the catalytic epoxidation of an alkene comprising contacting a transition metal substituted polyoxofluorometalate and molecular oxygen with said alkene.

6 Claims, 1 Drawing Sheet

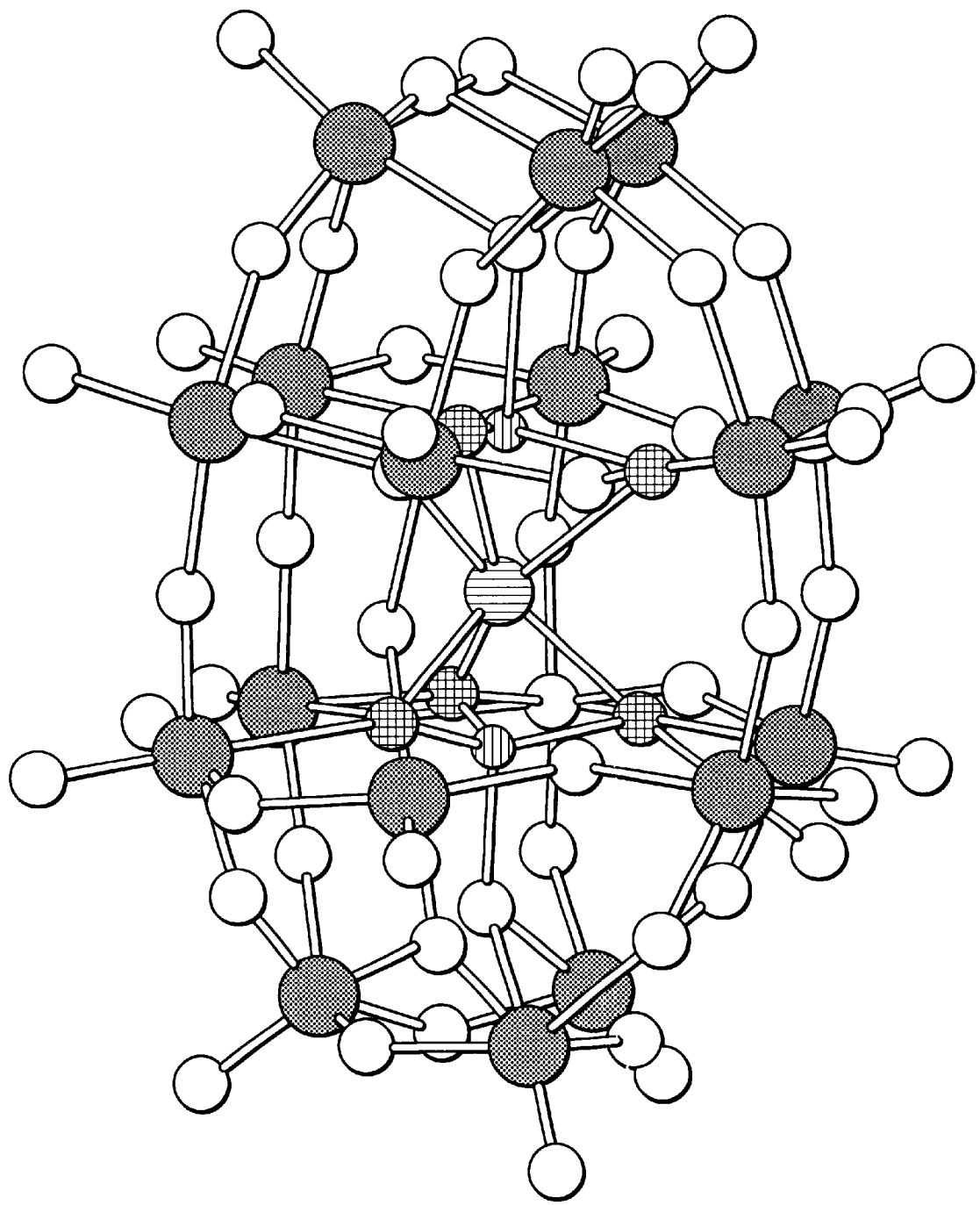

POLYOXOFLUOROMETALLATES AND USE THEREOF AS CATALYSTS FOR THE EPOXIDATION OF ALKENES

This application is the National Phase of International Application PCT/IL00/00044 filed Jan. 24, 2000 which designated the U.S. and that International Application was published under PCT Article 21(2) in English.

TECHNICAL FIELD

The present invention relates to the catalytic activation of molecular oxygen for alkene epoxidation using transition metal substituted polyoxofluorometalates as catalysts. More specifically, the present invention relates to a process for the catalytic epoxidation of alkene and to novel transition metal substituted polyoxofluorometalates utilizable therein.

BACKGROUND ART

Epoxidation of alkenes is an important chemical transformation whereby an oxygen atom is added to a carbon-carbon double bond to form an epoxide. Epoxides are often utilized as intermediate compounds which can then be transformed to final products. Examples include but are certainly not limited to ethylene glycol and polyethylene glycol from ethylene oxide, propylene glycol from propylene oxide, phenylacetaldehyde from styrene oxide and propranolol from 2R-glycidol.

Epoxidation of alkenes can be carried out using numerous techniques. The oldest and probably most common method is to react the alkene with an organic peracid, equation (1).

Equation (1)

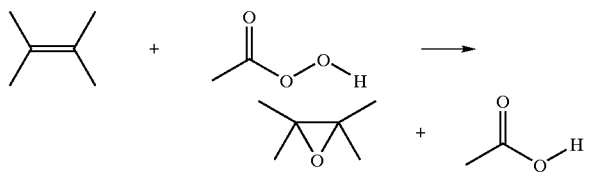

Typical peracids used in the art include perbenzoic acid, peracetic acid, performic acid, perphthalic acid and substituted perbenzoic acids such as 3-chloroperbenzoic acid. The salts of such acids may also be effective oxidants as in the case of magnesium monoperoxophthalate. The acids may be used as pure compounds or as prepared in situ in the reaction mixture by for example adding hydrogen peroxide to acetic anhydride to form peracetic acid. Although processes based on the reaction as described in equation (1) are known, there are certain drawbacks that are associated with such reactions. Among these one may cite (a) the propensity for formation of by-products such as glycols and glycol esters by reaction of the epoxide with water and/or acid in the reaction medium, (b) the necessity of recovering and/or recycling the acid co-product and (c) the necessity for stringent reaction control because of the safety danger involved in use of organic peracids (acyl hydroperoxides).

In order to minimize the danger in using peroxides as oxidants the use of alkyl and aryl hydroperoxides in place of acyl hydroperoxides has been suggested. and applied. These oxidants do not normally react with alkenes and the addition of a catalyst is required as described in equation (2).

Equation (2)

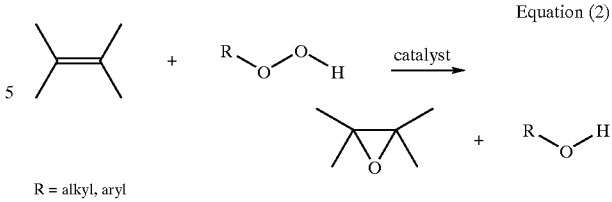

R = alkyl, aryl

Some hydroperoxides commonly used in such reactions are tert-butylhydroperoxide, cumene hydroperoxide and ethylbenzene hydroperoxide. The catalysts used are most commonly based on compounds containing Ti(IV), V(V), Mo(VI) or W(VI) although many compounds based on other metals have been described as being effective catalysts. These reactions are safer because of the lower reactivity of alkyl and aryl hydroperoxides compared to organic peracids, however, the other disadvantages associated with the use of acyl hydroperoxides remain. Thus, reactions are not necessarily more selective for the presence of catalysts and often lead to additional side reactions, for example substitution and oxidation at the allylic carbon of the alkene instead of oxygen addition to the double bond. Similarly to the use of acyl hydroperoxides, the alcohol co-product must be recovered, recycled and/or otherwise utilized.

A further method to epoxidize alkenes is to use aqueous hydrogen peroxide as oxidant as shown in equation (3).

Equation (3)

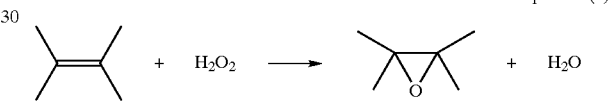

Such a reaction representss a conceptual improvement compared to the use of organic hydroperoxides in that the co-product is water and therefore is environmentally benign and need not be recovered or recycled. As in the use of alkyl- and aryl hydroperoxides the presence of a catalyst is necessary, which are again often compounds containing Ti(IV), V(V), Mo(VI) or W(VI) among others. In only certain cases has high selectivity been reported for alkene epoxidation. Some effective and selective catalysts include titanium silicalite-1 and other titanium substituted zeolites, and polyoxometalates such as $[WZnMn_2(ZnW_9O_{19})_2]^{12-}$ and $\{PO_4[WO(O_2)_2]_4\}^{3-}$. In many cases, the use of hydrogen peroxide represents an ideal oxidant provided reactions are selective. An exception is in cases where the low price of the epoxide makes the use of hydrogen peroxide prohibitively expensive.

An additional important method for synthesis of epoxides from alkenes is via formation of a halohydrin, preferably a chlorohydrin, using hypochlorous acid in the first step, followed by use of base, eg NaOH, for ring closure in the second step, as described in equation (4).

Equation (4)

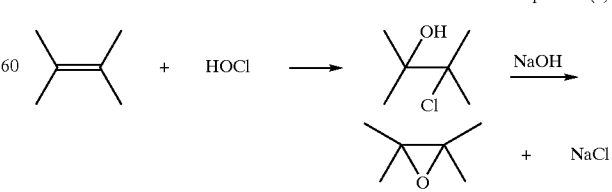

This is a very simple procedure which has, however, two problems. First, usually the presence of molecular chlorine in hypochlorous acid leads to formation of dichlorinated organics which are undesirable by-products and must be disposed of. Second, the process also forms large amounts of salts as co-product which also must be treated or recycled.

The ideal oxidant for alkene epoxidation both from an ecological and economic point of view would be molecular oxygen (dioxygen) as found in air. The addition of dioxygen to an alkene is disfavored kinetically, thus catalytic procedures need to be applied. In cases where there is no allylic carbon to the double bond, oxygen may be added to the double bond using a silver catalyst at elevated temperatures. In this way, ethylene oxide is manufactured from ethylene. For similar procedures with other alkenes, such as 1-butene, propene etc. this reaction fails to give epoxide in significant amounts. The basic problem in use of dioxygen for epoxidation of alkene lies in the radical nature of the molecular oxygen molecule. In homogeneous reactions, this radical nature always leads to a preferred radical reaction via substitution of hydrogen at an allylic carbon atom. Therefore, the common mode of utilization of dioxygen in liquid phase catalyzed reactions does not yield epoxide as major product. The situation in gas phase reactions is similar whereby activation of alkenes leads to allylic type carbocations, carbanions or carbon radicals again preventing formation of epoxides as a significant product.

Conceptually, in order to use dioxygen for alkene epoxidation, activation of dioxygen should be via formation of a high valent metal oxo compound formed after scission of the oxygen-oxygen bond. These high valent metal-oxo intermediates are effective epoxidizing agents. Most commonly this is carried out in nature by use of monooxygenase type enzyme such as cytochrome P-450 or methane monooxygenase. Such enzymes may be mimicked for example by using manganese and iron porphyrins as catalysts. The monooxygenase mechanism, however, requires two electrons from a reducing agent in order to cleave the oxygen-oxygen bond leading to formation of the high valent metal-oxo intermediate active in alkene epoxidation. From a process point of view the reducing agent becomes the limiting reagent instead of dioxygen and negates the attractivity of such a process.

The alternative is activation of dioxygen in a dioxygenase type mechanism. In such a reaction, dioxygen is cleaved using two metal centers leading to formation of two high valent metal-oxo species. This type of reaction has been until recently only realized using a ruthenium substituted tetramesitylporphyrin (RuTMP). Turnover rates to epoxide are very low and the catalyst has limited stability.

The limited stability of porphyrin ligands has led to the suggestion that transition metal substituted polyoxometalates be important alternative catalysts to metalloporphyrins as disclosed and discussed in Hill, U.S. Pat. No. 4,864,041. Transition metal substituted polyoxometalates are compounds of the general formula $X_x(TM)_yM_mO_z^{q-}$ where the heteroatom, X, if present (x-0) may be main group or transition metals, the addenda atoms, M, are molybdenum, tungsten, niobium or vanadium or a combination thereof, and TM is one or several different transition metals. Several different structure types are known. These catalysts would retain the high activity of their metalloporphyrin counterparts, however, are significantly more thermally and oxidatively stable, thus allowing their use as long living catalysts.

The previous work of U.S. Pat. No. 4,864,041 describes the application of transition metal substituted polyoxometalates for the epoxidation of alkenes using oxygen donors such a iodosylbenzene. Other reported academic research has evolved from this report and has described alkene epoxidation using other oxygen donors such as tert-butylhydroperoxide, hydrogen peroxide and p-cyano-N,N-dimethylaniline-N-oxide ("Polyoxometalate Complexes in Organic Oxidation Chemistry", R. Neumann, *Prog. Inorg. Chem.* 1998, 47, 317–370.). The use of transition metal substituted polyoxometalates as catalysts for alkene epoxidation with molecular oxygen has been recently described ("A Process for the Epoxidation of Alkenes" R. Neumann and M. Dahan, PCT Publication No. WO 98/54165, "Molecular Oxygen Activation: A Ruthenium Substituted Polyoxometalate as an Inorganic Dioxygenase Catalyst" R. Neumann and M. Dahan, *Nature,* 1997, 388, 353–355, and "Molecular Oxygen Activation by a Ruthenium Substituted "Sandwich" Type Polyoxometalate" R. Neumann and M. Dahan, *J. Am. Chem. Soc.,* 1998, 120, 11969–11976.) In these works it was shown that transition metal substituted polyoxometalates, especially $Q_{11}WZnRu_2(ZnW_9O_{19})_2$ where Q is quaternary ammonium such as triocaprylmethyl ammonium can be used to activate molecular oxygen in a dioxygenase mode. Thus reaction of $Q_{11}WZnRu_2(ZnW_9O_{19})_2$ with molecular oxygen leads to an intermediate species thought to be a ruthenium(IV)-oxo moiety capable of transferring oxygen to an alkene to yield an epoxide.

This process in general requires two separate reaction stages which limits its utility, first the reaction of $Q_{11}WZnRu_2(ZnW_9O_{19})_2$ with molecular oxygen and then second the reaction with an alkene to yield an epoxide.

DISCLOSURE OF THE INVENTION

Accordingly, it is an object of this invention to provide a process for the catalytic one stage epoxidation of alkenes using molecular oxygen as oxidant utilizing transition metal substituted polyoxofluorometalates. It is also an object of this invention to provide a method for preparing some transition metal substituted polyoxofluorometalates. It is a further objective of this invention to provide new transition metal substituted polyoxofluorometalates.

Thus, according to the present invention there is now provided a process for the catalytic epoxidation of an alkene comprising contacting a transition metal substituted polyoxofluorometalate and molecular oxygen with said alkene.

In preferred embodiments of the present invention said process is carried out with a polyoxofluorometalate of the general formulas Ia: $Q_q[X_x(TM)_y(O)_yM_mF_nO_z]^q$ or Ib: $Q_q[X_x(TM)_y(H_2O)_yM_mF_nO_z]^q$, wherein X is selected from the group consisting of H, alkali metal, alkaline earth metal, main group element and transition metal, and combinations thereof, M is selected from the group consisting of molybdenum, tungsten, niobium, vanadium and combinations thereof, TM is a transition metal, x is 0, or 16, y is 14, m is 4–200, n is 1–10, and z is 5–600, and Q is a countercation countering the charge $q^-$, said countercation being any suitable cation including, but not being limited to, alkali and alkaline earth metal ions, unsubstituted and substituted quaternary ammonium, phosphonium or arsenium cations, and the like. In preferred embodiments, the countercation is an alkali metal cation such as Na or K or substituted quaternary ammonium such as tricaprylmethyl ammonium.

As used herein in the specification and claims, the term "alkali metal" includes Na, K, Li, Rb and Cs, and is preferably Na; the term "alkaline earth metal" includes Ca, Ba, Mg and Sr; the term "main group element" includes all elements of columns IIIa, IVa, Va and VIa of the Periodic Chart of the Elements such as, but not limited to, B, Al, Ga, C, Si, Ge, Sn, Pb, P, As, Sb, Bi, S, Se and Te; the term "transition metal" includes all transition elements of columns Ib to VIIb and VIII of the Periodic Chart of the Elements and, when referring to the definition of X, includes preferably, without being limited to, Sc, Ti, V, Cr, Mn, Fe, Co, Ni, Cu, Zn, Y, Zr and Cd, and when referring to the definition of TM, includes preferably, without being limited to, Ti, V, Cr, Mn, Fe, Co, Ni, Cu, Zn and the noble metals Ru, Pd, Rh, Ir, Os and Pt. In preferred embodiments, the transition metal TM is selected from Ti, V, Ru, Pt, Pd, Os, Ir and Rh, and is most preferably Ru.

In one preferred embodiment of this aspect of the invention, the polyoxofluorometalates used in the catalytic epoxidation of alkenes, have the general formulas Ia' $Q_q[NaH_2(TM)(O)M_{17}F_6O_{55}]^q$ and Ib' $Q_q[NaH_2(TM)(H_2O)M_{17}F_6O_{55}]^q$ and the molecular structure depicted in FIG. 1, wherein the circle with horizontal lines denotes Na, the empty circles denote oxygen, the circles with both horizontal and vertical lines denote F, the circles with vertical lines denote H, and the full circles denote metal M atoms selected from Mo, W, Nb, V or combinations thereof and 14 transition metal TM atoms including preferably, without being limited to, Ti, V, Cr, Mn, Fe, Co, Ni, Cu, Zn and the noble metals Ru, Pd, Rh, Ir, Os and Pt. In one preferred embodiment, the metal atom M is tungsten (W) and the transition metal is Ru and the polyoxofluorometalate has the formula $Q_9[NaH_2(Ru)(H_2O)W_{17}F_6O_{55}]^9$.

In another aspect of the invention, there is provided a two-step method for the preparation of the polyoxofluorometalates of the general formula Ib' above, said method comprising the steps of:
(i) preparing a polyoxofluorometalate of the formula Ib', wherein M is W and TM is Zn, by reaction of a tungstate with HF and addition of a Zn salt such as zinc acetate to the mixture reaction; and
(ii) replacing the Zn in the polyoxofluorometalate obtained in step (i) by addition of a salt of a transition metal including preferably, without being limited to, Ti, V, Cr, Mn, Fe, Co, Ni, Cu, Zn and the noble metals Ru, Pd, Rh, Ir, Os and Pt.

Examples of transition metal salts that can be used according to the invention include, but are not limited to, $VOSO_4$, Mn acetate, Ni nitrate, Co nitrate, and the Ru salt with dimethylsulfoxide $Ru(DMSO)_4Cl_2$.

Compounds of the formula Ib' above wherein the transition metal TM is Zn, Co, Ni, Mn and Fe are known (Wasfi et al., Inorg. Chem. 1991, 30, 1788; Jorris, T. L., Ph. D. Thesis, Georgetown University, 1987). These compounds, wherein the transition metal TM is Co, Ni, Mn and Fe, were prepared by a one-step method different from the two-step method of the present invention and it is not certain whether their structure is identical to the structure of the compounds of the formula Ib' of the present invention wherein TM is Co, Ni, Mn and Fe.

Thus, a third aspect of the present invention relates to new polyoxofluorometalates of the general formula Ib' $Q_q[NaH_2(TM)(H_2O)M_{17}F_6O_{55}]^q$ and the molecular structure depicted in FIG. 1, wherein the circle with horizontal lines denotes Na, the empty circles denote oxygen, the circles with both horizontal and vertical lines denote F, the circles with vertical lines denote H, and the full circles denote metal. M atoms selected fron Mo, W, Nb, V or combinations thereof and 1–4 transition metal TM atoms selected from Ti, V, Cr, and the noble metals Ru, Pd, Rh, Ir, Os and Pt. In one preferred embodiment, the metal atom M is tungsten (W) and the transition metal is Ru and the polyoxofluorometalate has the formula $Q_9[NaH_2(Ru)(H_2O)W_{17}F_6O_{55}]^9$.

As indicated above, the process of the present invention relates to (a) the preparation of transition metal substituted polyoxofluorometalates (TMSPFOM) to (b) catalyze the epoxidation of alkenes with molecular oxygen, according to equation (5).

Equation (5)

Polyoxofluorometalates are mixed oligomeric oxides and fluorides of defined structure based on addenda of tungsten, molybdenum, niobium or vanadium or a combination thereof. More specifically, transition metal substituted polyoxofluorometalates are compounds of the general formulas Ia or Ib described hereinbefore. The specific class depicted in FIG. 1, of transition metal substituted polyoxofluorometalates, $[TM(H_2O)H_2F_6NaW_{17}O_{55}]^{q-}$, prepared and used in the process of the present invention are characterized as having a central core containing six fluorine atoms replacing oxygen atoms usually found in polyoxometalates. Other transition metal substituted polyoxofluorometalates of the formula $[TM(H_2O)W_{11}F_xO_{39-x}]^{q-}$ where x=1–6 can also be used. The transition metal cations are assumed to be positioned at terminal positions and are hexacoordinate with at least one labile ligand such as water. The preferred transition metal substituted polyoxofluorometalate for this process is $[Ru(H_2O)H_2F_6NaW_{17}O_{55}]^{9-}$. No transition metal substituted polyoxofluorometalate or more specifically those of the general structure described and shown above have ever been used as catalysts for the epoxidation of alkenes with molecular oxygen.

The catalytic reaction as described in equation (5) is carried out by contacting the catalyst with moecular oxygen and alkene. The catalyst is contacted simultaneously with both the molecular oxygen and alkene. The reaction or contact between the catalyst and reactants (alkene and molecular oxygen) may take place in a solvent whereby the reactants are added to the catalyst dissolved in a liquid phase. Some typical solvents are aliphatic, aromatic or halogenated hydrocarbons. Some exemplary solvents of these classes are 1,2-dichloroethane, heptane, toluene, xylene, chlorobenzene or mixtures thereof. Alternatively, the catalyst may be placed on a support or used as a simple solid followed by addition of the reactants. The support used for the catalyst may be any support used in heterogeneous catalysis including among others silica, alumina and other oxides.

The alkenes applicable as reactants in this process may be any type of alkenes known. This includes simple terminal and linear alkenes such as ethene, propene, 1-butene, 1-octene etc. The alkene may be an internal branched or linear alkene such as 2-butene, 2-octene, 2-methyl-2-heptene, 2,3-dimethyl-2-butene, etc. The alkene may also be cyclic for example cyclohexene, cyclooctene, norbornene, etc. Molecular oxygen may be used pure, as air, as oxygen enriched air, or as oxygen depleted air. Inert gases may be added. The suggested temperature range. of the reaction is between 0 and 300° C., more preferably between 25 and 250° C. and most preferably between 60 and 180° C. The reaction may be operated at atmospheric, sub-atmospheric or super-atmospheric pressures. Most preferably the reaction is run at super-atmospheric pressures.

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

DESCRIPTION OF PREFERRED EMBODIMENTS

EXAMPLES

A. Preparation of polyoxofluorometalates

1. $K_9[Zn(H_2O)H_2F_6NaW_{17}O_{55}]$ was prepared as follows (according to Thomas L. Jorris, Ph.D. dissertation, 1987): 44 g of $NaWO_4 \times 2H_2O$ were dissolved in 100 mL of water in a teflon beaker and brought to 80° C.. 49% HF was added dropwise until the pH became 4.5. The white precipitate was filtered off and the filtrate was reheated to 80° C. Seven grams of $Zn(OOCCH_3)_2$ dissolved in 5 mL water were added slowly while keeping the pH at 4.5. The solution was stirred an additional hour at 80° C. and cooled followed by the addition of 3 g of KCl. The white precipitate was filtered and recrystallized from water, yield 9.6 g.

2. $K_7[H_2F_6NaVW_{17}O_{56}]$ was prepared as follows: 0.326 g of $VOSO_4$ dissolved in 5 mL of an acetate buffer (pH 5) was added slowly to a solution of 4.8 g $K_9[Zn(H_2O)H_2F_6NaW_{17}O_{55}]$ in 40 mL of an acetate buffer (pH=5) at 50° C. The solution turned purple immediately. After stirring for 30 minutes, the solution was cooled and filtered. To the filtrate a saturated KCl solution was added and the precipitate formed was filtered and recrystallized, yield 2.4 g.

3. $K_9[Mn(H_2O)H_2F_6NaW_{17}O_{55}]$ was prepared as follows: 0.4 g of manganese acetate tetrahydrate dissolved in 5 mL of an acetate buffer (pH=5) was added slowly to a solution of 4.8 g $K_9[Zn(H_2O)H_2F_6NaW_{17}O_{55}]$ in 40 mL of an acetate buffer (pH=5) at 50° C. The solution turned pink immediately. After stirring for 30 minutes, the solution was cooled and filtered. To the filtrate a saturated KCl solution was added and the precipitate formed was filtered and recrystallized, yield 3 g.

4. $K_9[Ni(H_2O)H_2F_6NaW_{17}O_{55}]$ was prepared as follows: 0.4 g of nickel nitrate hexahydrate dissolved in 5 mL of an acetate buffer (pH=5) was added slowly to a solution of 4.8 g $K_9[Zn(H_2O)H_2F_6NaW_{17}O_{55}]$ in 40 mL of an acetate buffer (pH 5) at 50° C. The solution turned light green immediately. After stirring for 30 minutes, the solution was cooled and filtered. To the filtrate a saturated KCl solution was added and the precipitate formed was filtered and recrystallized, yield 0.35 g.

5. $K_9[Co(H_2O)H_2F_6NaW_{17}O_{55}]$ was prepared as follows: 0.4 g of cobalt nitrate hexahydrate dissolved in 5 mL of an acetate buffer ($pH_5$) was added slowly to a solution of 4.8 g $K_9[Zn(H_2O)H_2F_6NaW_{17}O_{55}]$ in 40 mL of an acetate buffer (pH=5) at 50° C. The solution turned dark red immediately. After stirring for 30 minutes, the solution was cooled and filtered. To the filtrate a saturated KCl solution was added and the precipitate formed was filtered and recrystallized, yield 2 g.

6. $K_9[Ru(H_2O)H_2F_6NaW_{17}O_{55}]$ was prepared as follows: 0.43 g of $Ru(DMSO)_4Cl_2$ dissolved in 50 mL of an acetate buffer (pH=5) was added slowly to a solution of 4.8 g $K_9[Zn(H_2O)H_2F_6NaW_{17}O_{55}]$ in 40 mL of an acetate buffer (pH=5) at 50° C. The solution turned light brown immediately. After stirring for 5 hours at 60° C., the solution was cooled and filtered. To the filtrate a saturated KCl solution was added and the precipitate formed was filtered and recrystallized, yield 1.7 g.

7. $Q_9[Ru(H_2O)H_2F_6NaW_{17}O_{55}]$ where Q is tricaprylmethyl ammonium was prepared by dissolving 1 mmol $K_9[Ru(H_2O)H_2F_6NaW_{17}O_{55}]$ of Example 6 above in 100 mL water, and 9 mmol tricaprylmethyl ammonium chloride dissolved in 75 mL dichloromethane were added. The phases were mixed vigorously for 30 min. The organic phase was separated, dried with sodium sulfate and the solvent was evaporated off. The yield was 98%.

B. Epoxidation of Alkenes

1. A 1 ml solution of degassed 1,2-dichloroethane containing 1 mmol cyclooctene and 10 µmol $Q_9[Ru(H_2O)H_2F_6NaW_{17}O_{55}]$ where Q is tricaprylmethyl ammonium was kept under 1.5 atm molecular oxygen at 80° C. for 24 hours. After cooling the solution, analysis of the solution showed a 88.5 % conversion to cyclooctene oxide.

2. A 1 ml solution of degassed 1,2dichloroethane containing 1 mmol 1-octene and 10 µmol $Q_9[Ru(H_2O)H_2F_6NaW_{17}O_{55}]$ where Q is tricaprylmethyl ammonium was kept under 1.5 atm molecular oxygen at 80° C. for 24 hours. After cooling the solution, analysis of the solution showed a 8.5 % conversion to 1-octene oxide.

3. A 1 ml solution of degassed 1,2-dichloroethane containing 1 mmol 1-octene and 10 µmol $Q_9[Ru(H_2O)H_2F_6NaW_{17}O_{55}]$ where Q is tricaprylmethyl ammonium was kept under 1.5 atm molecular oxygen at 120° C. for 24 hours. After cooling the solution, analysis of the solution showed a 22.1 % conversion to 1-octene oxide.

4. A 1 ml solution of degassed 1,2-dichloroethane containing 1 mmol 1-decene and 10 µmol $Q_9[Ru(H_2O)H_2F_6NaW_{17}O_{55}]$ where Q is tricaprylmethyl ammonium. was kept under 1.5 atm molecular oxygen at 120° C. for 24 hours. After cooling the solution, analysis of the solution showed a 24.3 % conversion to 1-decene oxide.

5. A 1 ml solution of degassed 1,2-dichloroethane containing 1 mmol 2-octene and 10 µmol $Q_9[Ru(H_2O)H_2F_6NaW_{17}O_{55}]$ where Q is tricaprylmethyl ammonium was kept under 1.5 atm molecular oxygen at 120° C. for 24 hours. After cooling the solution, analysis of the solution showed a 33.4 % conversion to 2-octene oxide.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. In a process for the catalytic epoxidation of an alkene by contacting the alkene with molecular oxygen in the presence of an epoxidation catalyst, the improvement wherein the catalyst is a transition metal substituted polyoxofluorometalate.

2. A process according to claim 1, wherein said polyoxofluorometalate is of the general formulas Ia, $Q_q[X_x(TM)_y(O)_yM_mF_nO_z]$ or Ib $Q_q[X_x(TM)_y(H_2O)_yM_mF_nO_z]^q$ wherein X is selected from the group consisting of H, alkali metal, alkaline earth metal, main group element and transition metal, and combinations thereof, M is selected from the group consisting of molybdenum, tungsten, niobium, vanadium and combinations thereof, TM is a transition metal, x is 0, or 1–6, y is 1–4, m is 4–200, n is 1–10, and z is 5–600, and Q is a countercation countering the charge $q^-$.

3. A process according to claim 1 or 2, wherein said transition metal TM is selected from Ti, V, Cr, Mn, Fe, Co, Ni, Cu, Zn and the noble metals Ru, Pd, Rh, Ir, Os and Pt.

4. A process according to claim 3, wherein said transition metal TM is selected from Ti, V, Ru, Pt, Pd, Os, Ir and Rh.

5. A process according to any one of claims to 1 to 4, wherein said polyoxofluorometalate has the general formula Ia' $Q_q[NaH_2(TM)(O)M_{17}F_6O_{55}]^q$ and Ib' $Q_q[NaH_2(TM)(H_2O)M_{17}F_6O_{55}]^q$ and the molecular structure depicted in FIG. 1, wherein the circle with horizontal lines denotes Na, the empty circles denote oxygen, the circles with both horizontal and vertical lines denote F, the circles with vertical lines denote H, and the full circles denote metal M atoms selected from Mo, W, Nb, V or combinations thereof and 1–4 transition metal TM atoms selected from Ti, V, Cr, and the noble metals Ru, Pd, Rh, Ir, Os and Pt, and Q is a countercation.

6. A process according to any one of claims 1 to 5, wherein said transition metal is ruthenium.

* * * * *